(12) United States Patent
Prais et al.

(10) Patent No.: US 9,994,477 B2
(45) Date of Patent: Jun. 12, 2018

(54) METHOD FOR REDUCING OR ELIMINATING RESIDUE IN A GLASS CONTAINER AND A GLASS CONTAINER MADE IN ACCORDANCE THEREWITH

(71) Applicant: Becton, Dickinson and Company, Franklin Lakes, NJ (US)

(72) Inventors: Alfred W. Prais, Hewitt, NJ (US); Bruno Cocheteux, Voiron (FR); Arturo Cortes, Estado de Mexico (MX); Patrice Delabie, Cold Spring, NY (US); Edouard Wales, Poisat (FR); Richard D. Luedtka, Columbus, NE (US); Randy Schaecher, Columbus, NE (US); Daniel Vulliet, Saint Paul de Varces (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days. days.

(21) Appl. No.: 14/853,276

(22) Filed: Sep. 14, 2015

(65) Prior Publication Data

US 2016/0002087 A1 Jan. 7, 2016

Related U.S. Application Data

(63) Continuation of application No. 11/664,236, filed as application No. PCT/US2005/035710 on Sep. 30, 2005, now abandoned.
(Continued)

(51) Int. Cl.
C03B 23/00 (2006.01)
C03B 23/09 (2006.01)
(Continued)

(52) U.S. Cl.
CPC ............ *C03B 23/092* (2013.01); *A61J 1/00* (2013.01); *A61M 5/3129* (2013.01); *A61M 5/3134* (2013.01); *A61M 5/34* (2013.01)

(58) Field of Classification Search
None
See application file for complete search history.

(56) References Cited

U.S. PATENT DOCUMENTS 1,999,525 A 4/1935 Morscholz
2,090,861 A 8/1937 Eisele
(Continued)

FOREIGN PATENT DOCUMENTS

DE 4326143 A1 12/1993
DE 4440702 A1 7/1996
(Continued)

OTHER PUBLICATIONS

Corning, "Properties of Pyrex, PyrexPlus, and Low Actinic Pyrex Cose 7740 Glass", http://www.quartz.com/pxprop.pdf, Accessed Sep. 4, 2017.*
(Continued)

*Primary Examiner* — Cynthia Szewczyk
(74) *Attorney, Agent, or Firm* — The Webb Law Firm

(57) ABSTRACT

A method of preparing a glass medical container is provided including the steps of providing a glass blank and forming a channel through a part of the glass blank, the channel being substantially free of tungsten or derivatives thereof. In a further aspect of the subject invention, a glass medical container is provided including a glass body having a channel extending through a part of the glass body, the channel being substantially free of tungsten or derivatives thereof. With the subject invention, tungsten or derivatives thereof can be generally or altogether completely avoided in glass medical containers.

16 Claims, 1 Drawing Sheet

Related U.S. Application Data

(60) Provisional application No. 60/614,914, filed on Sep. 30, 2004.

(51) Int. Cl.
*A61M 5/31* (2006.01)
*A61J 1/00* (2006.01)
*A61M 5/34* (2006.01)

(56) References Cited

U.S. PATENT DOCUMENTS

| | | | | |
|---|---|---|---|---|
| 2,188,636 | A * | 1/1940 | Vilensky | C03B 5/1672 420/468 |
| 2,190,296 | A | 2/1940 | Richardson | |
| 2,306,995 | A | 12/1942 | Palmer et al. | |
| 2,368,170 | A | 1/1945 | Smith | |
| 2,583,431 | A | 1/1952 | Laidig et al. | |
| 3,973,717 | A * | 8/1976 | Jensen | B21C 37/0803 228/144 |
| 4,118,237 | A * | 10/1978 | Beall | C03B 32/02 501/10 |
| 4,388,094 | A | 6/1983 | Carpenter et al. | |
| 4,541,474 | A | 9/1985 | Pecci | |
| 5,312,577 | A | 5/1994 | Peterson et al. | |
| 5,779,753 | A * | 7/1998 | Vetter | B23K 26/0081 65/105 |
| 6,216,493 | B1 | 4/2001 | Weston et al. | |
| 6,341,502 | B2 | 1/2002 | Delgado-Carranza et al. | |
| 6,415,631 | B1 | 7/2002 | Weston et al. | |
| 6,679,085 | B1 | 1/2004 | Singer et al. | |
| 2002/0078713 | A1 | 6/2002 | Matsumoto et al. | |
| 2004/0065116 | A1 * | 4/2004 | Vetter | B23K 26/0081 65/29.19 |
| 2006/0016220 | A1 * | 1/2006 | Spaeth | C03B 27/06 65/114 |

FOREIGN PATENT DOCUMENTS

| | | |
|---|---|---|
| DE | 1224002 B | 9/1996 |
| DE | 19644673 A1 | 4/1998 |
| EP | 0443794 A1 | 8/1991 |
| EP | 0867418 A1 | 9/1998 |
| EP | 1133452 B1 | 9/2002 |
| EP | 1394124 A1 | 3/2004 |
| EP | 1471040 A1 | 10/2004 |
| GB | 526688 | 9/1940 |
| GB | 600667 | 4/1948 |
| JP | 11322350 | 11/1999 |
| JP | 2003238172 A1 | 8/2003 |
| WO | 0136341 A2 | 5/2001 |

OTHER PUBLICATIONS

Wakisaka et al., "Rapid analysis for the heavy metals limit test by energy-dispersive X-ray fluorescence analysis with monochromatic excitation," Bunseki Kagaku, 1996, vol. 45, No. 11, pp. 1025-1031.

Wang et al., "Determination of tungsten in bulk drug substance and intermediates by ICP-AES and ICP-MS," Journal of Pharmaceutical and Biomedical Analysis, 1999, vol. 19, pp. 937-943.

Darling, Iridium Platinum Alloys: A Critical Review of their Constitution and Properties, Platinum Metals Rev., 1960, vol. 4:1, pp. 18-26.

Platinlegierungen, Lexikon de Chemie, 1998, www.spektrum.de/lexikon/chemie/platinlegierungen/7220.

Franke, Lueger Lexikon der Technik, 1963, pp. 374-375, Relevance: provides an explanation of the roles of various alloying elements in steel.

Stainless steel, The New Encyclopaedia Britannica, 1994, vol. 11, p. 203.

Stokes, Platinum in the Glass Industry: ZGS Materials Supplement Conventional Alloys, Platinum Metals Rev., 1987, vol. 31,2, pp. 54-62.

Surpi Stainless Steels, 2011, pp. 24-26, Relevance: provides an explanation of the roles of various alloying elements in stainless steel.

Werkstoffdatenblatt Alloy 600, Hempel Special Metals, 2015, http://alloy600.hempel-metals.com.

Shott Guide to Glass, 1996, pp. 51, 52, 84, and 85.

\* cited by examiner

METHOD FOR REDUCING OR ELIMINATING RESIDUE IN A GLASS CONTAINER AND A GLASS CONTAINER MADE IN ACCORDANCE THEREWITH

CROSS-REFERENCES TO RELATED APPLICATIONS

This application is a continuation of U.S. patent application Ser. No. 11/664,236, filed Dec. 28, 2007, which is a National Stage Application under 35 U.S.C. § 371 of PCT International Application No. PCT/US2005/035710, filed Sep. 30, 2005, which claims priority to U.S. Provisional Application No. 60/614,914, filed Sep. 30, 2004, the entire disclosures of each of which are incorporated by reference herein.

BACKGROUND OF THE INVENTION

This invention relates to a method for reducing tungsten and derivatives thereof in a glass container and to a glass container with reduced tungsten and derivatives thereof.

Tungsten and derivatives thereof have been commonly used in glass forming techniques. In particular, tungsten-containing pins have been used in forming shaped apertures or channels in glass structures. As used herein, the term "tungsten-containing" means tungsten, tungsten plus one or more other materials, or one or more other materials plus tungsten, in any combination and percentage. Tungsten has a high fusion temperature relative to glass and is well suited for glass manufacturing. Typically, a tungsten-containing pin is used to form an aperture or channel in a glass container, with the glass being thermally and/or mechanically manipulated about the pin and into conforming engagement therewith. An iterative process can be used where a plurality of pins are used sequentially to gradually form the aperture or channel in a sequence of manipulations to the glass. With removal of the final pin, a finished aperture or channel is left in the glass structure. This technique has been commonly used in the formation of glass medical containers, including glass syringe barrels, glass vials, and glass drug cartridge bodies. Each of the glass medical containers (glass syringe barrels, glass vials and glass drug cartridge bodies) includes a reservoir for containing a drug, and a channel in communication with the reservoir to provide a means of accessing or removing the drug from the reservoir, typically via a cannula or similar liquid communication means.

It has been found that tungsten-containing pins undesirably leave a tungsten-containing residue on the formed glass structures, particularly, portions that had been in contact with the pins, for example, the aperture or channel. The tungsten-containing residue may have detrimental effects on any substance contained or stored within the glass medical container. First, tungsten or derivatives thereof may be deposited as particulate matter on an inner surface of the aperture or channel, and such particulate matter may be visible in the contained substance. Certain medical procedures require a medical practitioner to view the procedure under magnification, including the administration of a drug from a glass medical container. The presence of such particulate matter may be dangerous to the patient and may also be disconcerting to the medical practitioner. Second, drugs containing proteins may be adversely affected by exposure to the tungsten or derivatives thereof. Certain proteins are prone to clump or aggregate about tungsten or derivatives thereof. This clumping or aggregation may lead to a loss in efficacy or other undesirable effects of the drug. In addition, in certain situations, the clumping or aggregation may be so extreme that solid fragments may be seen by the naked eye and be disconcerting to a potential user.

Water washing glass medical containers is known in the prior art. Such washing techniques have been known to reduce or remove tungsten-containing residue. However, washing techniques have inherent limitations and cannot reliably and repeatedly remove all or substantially all tungsten and derivatives thereof from a glass medical container.

SUMMARY OF THE INVENTION

In one aspect of the subject invention, a method for preparing a glass medical container is provided including the steps of providing a glass blank and forming a channel through a part of the glass blank, the channel being substantially free of tungsten or derivatives thereof. In a further aspect of the subject invention, a glass medical container is provided including a glass body having a channel extending through a part of the glass body, the channel being substantially free of tungsten or derivatives thereof. With the subject invention, tungsten or derivatives thereof can be generally or altogether completely avoided in glass medical containers.

As used herein, a "drug" is an illustrative and non-limiting term and refers to any substance to be injected into a patient for any purpose; "tungsten or derivatives thereof" shall mean tungsten or any substance containing tungsten, including, but not limited to, tungsten salts and tungsten-containing alloys; and, "substantially free" shall mean a level of tungsten or derivatives thereof low enough to not detrimentally alter or affect a drug. For example, and by way of illustration and not limitation, substantially free may mean tungsten or derivatives thereof at a level that the tungsten or derivatives thereof is not visible, does not detrimentally alter the efficacy or otherwise adversely effect the drug, and/or does not detrimentally promote unacceptable levels of clumping or aggregation of proteins contained in the drug.

These and other features of the invention will be better understood through a study of the following detailed description and accompanying drawings.

DETAILED DESCRIPTION OF THE INVENTION

With the subject invention, a method is provided for substantially reducing or altogether eliminating tungsten or derivatives thereof from a glass container without the need for additional annealing, sterilization or washing steps after the container has been completely formed. The method is particularly well-suited for use in forming glass medical containers. For illustrative purposes, an exemplary glass medical container 10 is shown and described which is in the form of a glass syringe barrel. As can be appreciated by those skilled in the art and from the disclosure provided herein, the glass medical container 10 can be any glass body used for containing or storing a liquid and/or dry substance, including, but not limited to glass syringe barrels, glass vials, and glass drug cartridge bodies.

Figure 1:
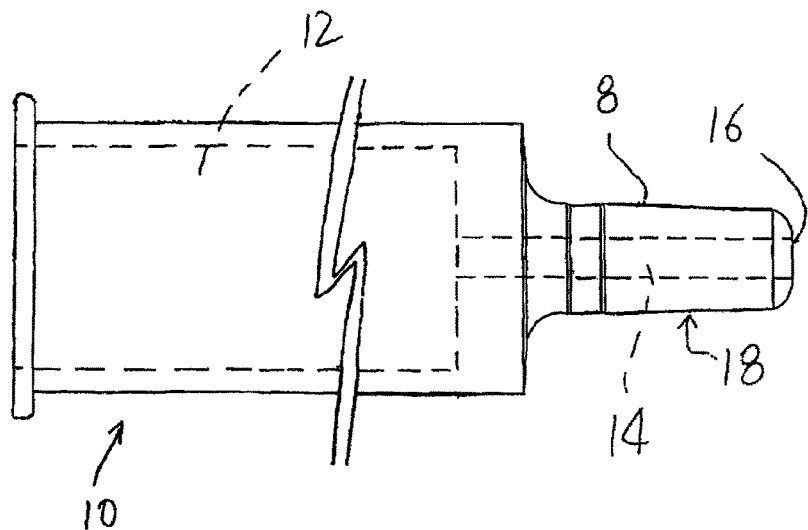
FIG. 1 is a plan view of an exemplary glass medical container in accordance with the subject invention.

With reference to FIG. 1, the glass medical container 10 defines a reservoir 12 and has a hub 8 with a channel 14 defined therethrough and in communication with the reservoir 12. The glass medical container 10 is preferably a unitary glass body. The channel 14 forms an aperture 16 at a distal end of the glass medical container 10. The channel 14, via the aperture 16, provides access to the reservoir 12 and any drug which may be contained therein. With the glass medical container 10 being a glass syringe barrel, the channel 14 is formed through the hub 8. The reservoir 12, as formed in the glass medical container 10, may partly define a volume for containing a drug. A piston, plunger, septum, tip cap, stopper, and so forth, may be used in connection with the glass medical container 10 to form a closed volume for containing a drug within the reservoir 12.

Figure 2:
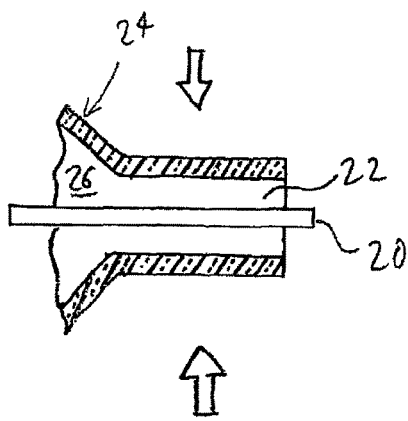
FIG. 2 is a schematic showing formation of a channel in a glass medical container.

With reference to FIG. 2, a process in accordance with the subject invention is depicted for forming the channel 14. In particular, a pin 20 is provided to form and extend into and possibly through an opening 22 defined in a glass blank 24. The glass blank 24 is a partially formed version of the glass medical container 10. For example, a glass blank 24 may comprise a generally cylindrical part having a substantially constant outer diameter, or it may be a partially or completely formed part having a portion through which the channel 14 is formed and defined. Thermal and mechanical manipulations are performed on and to the glass blank 24 to form the final glass medical container 10 as is known in the art. The opening 22 is in communication with reservoir 26 which ultimately, after full formation, results in the reservoir 12.

Figure 3:
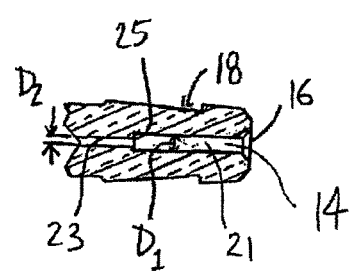
FIG. 3 is a partial cross-sectional view of an alternative channel shape formed in a glass medical container.

To form the channel 14, portions of the glass blank 24 about the opening 22 are manipulated, either in one process or in iterations, to force the portions of the glass blank 24 into conforming engagement with the pin 20. The manipulations may include mechanical manipulations (e.g., rolling or other shape forming processes) and/or thermal manipulations (e.g., heating glass to a malleable state). In this manner, the channel 14 is generally formed with a cross-sectional shape corresponding to the exterior surface of the pin 20. For example, as shown in FIG. 2, the pin 20 is shown with a constant cross-section along its length. Correspondingly, as shown in FIG. 1, the channel 14 also has a constant cross-section along its length. Alternative configurations for the channel 14 are possible. With reference to FIG. 3, the channel 14 is shown with varying cross-sections along its length. This configuration is preferred for staked needle configuration glass syringe barrels, while the constant cross-sectional configuration of FIG. 1 is preferred for Luer tip mounted needle configurations. With the configuration of FIG. 3, a first portion 21 of the channel 14 defines a substantially constant diameter D1, while a second portion 23 of the channel 14, located closer to the reservoir 12, defines a substantially constant diameter D2. The diameter D1 is larger than the diameter D2 with a step 25 being formed therebetween. The step 25 acts as a stop against an insertion of a needle during assembly. The needle is glued or otherwise secured within the first portion 21 and in communication with the second portion 23. The channel 14 can take on various configurations (e.g., more than two diameter changes, tapering, etc.), and, as is readily recognized, the pin 20 is shaped externally to achieve the desired configuration of the channel 14. Alternatively, a variety of the pins 20 having different diameters may be used to form a channel 14 as shown in FIG. 3, e.g., sequentially.

For typical applications where the glass medical container 10 is a glass syringe barrel, the channel 14 may have a configuration as in FIG. 1 with a continuous diameter of about 1.0 mm; or, the channel 14 may a configuration as in FIG. 3 with a diameter D1 of about 0.6 mm, and a diameter D2 in the range of 0.2 to 0.4 mm. Also, the channel 14, as is common with glass syringe barrels, defines a diameter smaller than the internal diameter defined by the reservoir 12. With a vial configuration or a drug cartridge body configuration, the channel 14 may have a diameter generally equal to the internal diameter of the reservoir 12, or even greater than the internal diameter of the reservoir 12.

For the avoidance of tungsten or derivatives thereof in the channel 14, it is preferred that the pin 20 be formed of a material that will not oxidize during the glass forming process described above. Generally, all materials can be oxidized, although special circumstances may be required for oxidation. With the glass forming process discussed above in connection with FIG. 2, the pin 20 may be thermally manipulated by exposure during thermal manipulation of the glass blank 24 to temperatures in the range of 600° C. to 900° C., and may be subjected to elevated pressures generated by shape-forming tools during mechanical manipulation of the glass blank 24. Under these conditions, tungsten oxidizes. Oxidation of prior art pins led to deposition of tungsten or derivatives thereof on portions of the glass blank 24 that were in contact with the pins, particularly the channel 14. In addition, the pin 20 is typically used in large scale, repetitious manufacturing and subjected to fast thermal cycles of heat application and removal, resulting in fatigue to the surface of the pin 20 and consequently, to the pin 20. Surface fatigue leads to weakening of the structure of the pin 20 and mechanical failure with fragments (typically microscopic) thereof breaking off during use of the pin 20 in the glass forming process and, consequently, to deposition of tungsten or derivatives thereof on and within the channel 14.

As indicated above, it is preferred that the pin 20 be formed of a material which does not oxidize when subjected to a glass forming process which is may be typically conducted under temperatures in the range of 600° C. to 900° C. and under elevated pressure caused by shape-forming tools. These conditions hereinafter shall be referred to as "glass forming process conditions." It will be obvious to persons skilled in the art that other conditions and parameters may be present during the process of forming a glass blank into a glass medical container. By way of non-limiting examples, materials that will not oxidize under the glass forming process conditions, and useable for the pin 20 in accordance with the present invention, include, but are not limited to, the following: metals or alloys containing platinum or platinum group metals; metals or alloys containing nickel; ceramics; silicides; and combinations thereof. It is preferred that the pin 20 be formed of a platinum/rhodium alloy with 80%-90% platinum and 20%-10% rhodium. With the pin 20 being formed of one of the aforementioned materials, or other material(s) that will not oxidize under the glass forming process conditions, deposition of tungsten or derivatives thereof on the glass medical container 10 due to the oxidation process can be avoided. As a result, the channel 14 can be formed substantially free of tungsten or derivatives thereof. It is also preferred that the pin 20 have a melting temperature above the melting temperature of the associated glass being formed into the glass medical container 10.

An alloy containing tungsten may be used to form the pin 20 where the tungsten-containing alloy does not oxidize under the glass forming process conditions. For example, the pin 20 may be formed of with a tungsten carbide which does not oxidize under the glass forming process conditions. To further minimize the amount of tungsten or derivatives thereof deposited in the channel 14 in accordance with this embodiment, it is preferred that the pin 20 be formed of a material containing a minimal amount of tungsten, even no tungsten.

In addition to selection of the material from which the pin 20 is made, the present invention may also control the environment in which the pin 20 is forming the channel 14 by introducing a controlling gas in the area of the pin 20 and channel 14. For example, the introduction of an inert gas such as nitrogen gas, by way of non-limiting example, in and around the area in which the pin 20 is used to reduce the oxygen content in that area can reduce oxidation of the pin 20.

As will be appreciated by those skilled in the art, the formation of the channel 14 may require various sequential forming steps including multiple pins 20, such as pins 20 of constant or varying diameters. For example, the channel 14 may be iteratively formed smaller over a sequence of forming stages with increasingly smaller diameter pins 20 being used. In each forming stage, the channel 14 is brought into conforming engagement with the associated pin 20, until a final forming stage is reached. All of the pins 20 used in the various stages in the formation of the channel 14 may be formed of the preferred materials described above. Alternatively, it has been found that certain forming stages may cause greater deposition of tungsten or derivatives thereof than other forming stages. For these critical forming stages, it is preferred that the pins 20 be formed of materials which do not oxidize under the glass forming process conditions and which do not include tungsten. The less critical forming stages may use pins formed of any material, including tungsten. With the glass medical container 10 being a glass syringe barrel and being subjected to multiple forming stages using a multiple of the pins 20, it is preferred that the last forming step utilize the pin 20 being formed of materials which do not oxidize under the glass forming process conditions and which do not include tungsten. The preceding forming stages may be formed of any material suitable for pin formation. The less critical forming stages may not expose the pin 20 to the same amounts of thermal and/or mechanical manipulation because the channel 14 is only roughly formed and thus may not contact the pin 20 to the same extent as may occur during the final forming stage(s).

With the subject invention, the channel 14 can advantageously be formed substantially free of tungsten or derivatives thereof. Using the following procedure for measuring concentration, it is preferred that the channel 14 have tungsten or derivatives thereof in an amount of 12 parts per billion or less. With the preferred process, not only is oxidation of the pin 20 avoided, but the pin 20 may be formed to not deposit tungsten or derivates thereof even under mechanical failure. This preferred process may produce glass medical containers which have undetectable levels of tungsten or derivatives thereof. These concentration levels are obtainable with the subject invention on large scale, industrial processes within highly acceptable tolerance levels. Prior art washing techniques have not been capable of obtaining such low levels on a repeated, widespread consistent basis.

Significantly, the subject invention is able to produce a glass medical container 10 that is substantially free tungsten or derivatives thereof without the need for additional annealing, sterilization or washing steps. With reference to FIG. 2, the glass blank 24 is an intermediate product that is both unsterilized and unwashed. Upon full formation, the glass medical container 10 may be subjected to annealing, sterilizing and air or liquid washing, although such further processing is not always carried out (such unsterilized containers being referred to as "bulk" processed containers). The sterilizing and washing steps may provide for additional removal of any residual tungsten or derivatives thereof which may be present. This residual tungsten or derivatives thereof may have come from the glass raw material, tooling which contacts the glass during formation, or tungsten pins used in the process. The aforementioned levels of tungsten or derivatives thereof, however, are achieved in accordance with the present invention without the additional annealing, sterilizing or washing processes.

Levels of tungsten or derivatives thereof may be measured by any technique. Different techniques may provide different results depending on how aggressively the tungsten or derivatives thereof is removed from the glass medical container for testing (i.e., more aggressive techniques remove higher levels of tungsten residue). With reference to Wang, et al., Journal of Pharmaceutical and Biomedical Analysis, 19 (1999) 937-943, "Determination of Tungsten in Bulk Drug Substance and Intermediates by ICP-AES and ICP-MS", a method of measuring levels of tungsten in drugs is described. Similar methodology can be used for measuring tungsten-containing residue levels. The inventors herein relied on the following procedure to measure the aforementioned levels of tungsten or derivatives thereof:

1. filling a glass medical container with purified water (e.g., prepared by laboratory purification system, Millipore Milli Ro 4) and sealing the glass medical container (e.g., with a tip cap);

2. placing the filled glass medical container into an ultrasonic bath containing water at ambient temperature for 60 minutes;

3. removing the glass medical container and dispensing the contained solution into a sample vessel; and, 4. measuring the concentration of the tungsten in the solution by Inductively Coupled Plasma Mass Spectrometry (ICP/MS).

The aforementioned levels of tungsten or derivatives thereof are actually measured concentration levels of tungsten in the extracted solution.

What is claimed is:

1. A method of producing a glass medical container comprising:
   providing a glass blank;
   providing a pin at an opening in said glass blank;
   heating said glass blank;
   introducing an inert gas into an environment surrounding said pin at least while the glass blank is being heated; and
   forming said glass blank to conformingly engage said pin to form a channel,
   wherein the pin comprises a metal selected from the group consisting of: platinum or platinum group metals; metals or alloys containing nickel; silicides; and combinations thereof.

2. The method of claim 1, wherein said forming step comprises forming said glass blank to form a channel having a length and defining a diameter that is constant along said length.

3. The method of claim 2, wherein said forming step comprises forming said glass blank to form a channel having a length and defining a diameter that varies along said length, and wherein said forming step comprises forming said glass blank to form a channel having a first portion defining a first constant diameter and a second portion defining a second constant diameter, said first diameter being larger than said second diameter.

4. The method of claim 3, wherein said first constant diameter is 0.6 mm and said second constant diameter is in the range of 0.2 to 0.4 mm.

5. The method of claim 1, wherein said forming step comprises thermally manipulating said glass blank at a temperature in the range of 600 to 900° C.

6. The method of claim 5, wherein said channel is substantially free of tungsten or derivatives thereof.

7. The method of claim 1, wherein said glass blank is unwashed before or after said forming step.

8. The method of claim 1, wherein the inert gas is nitrogen.

9. A method of producing a glass medical container comprising:
providing a glass blank;
providing a pin at an opening in said glass blank;
heating said glass blank;
introducing an inert gas into an environment surrounding said pin at least while the glass blank is being heated; and
forming said glass blank to conformingly engage said pin to form a channel.

10. The method of claim 9, wherein said forming step comprises forming said glass blank to form a channel having a length and defining a diameter that is constant along said length.

11. The method of claim 10, wherein said forming step comprises forming said glass blank to form a channel having a length and defining a diameter that varies along said length, and wherein said forming step comprises forming said glass blank to form a channel having a first portion defining a first constant diameter and a second portion defining a second constant diameter, said first diameter being larger than said second diameter.

12. The method of claim 11, wherein said first constant diameter is 0.6 mm and said second constant diameter is in the range of 0.2 to 0.4 mm.

13. The method of claim 9, wherein said forming step comprises thermally manipulating said glass blank at a temperature in the range of 600 to 900° C.

14. The method of claim 13, wherein said channel is substantially free of tungsten or derivatives thereof.

15. The method of claim 9, wherein said glass blank is unwashed before or after said forming step.

16. The method of claim 9, wherein the inert gas is nitrogen.

* * * * *

UNITED STATES PATENT AND TRADEMARK OFFICE
CERTIFICATE OF CORRECTION

PATENT NO. : 9,994,477 B2
APPLICATION NO. : 14/853276
DATED : June 12, 2018
INVENTOR(S) : Alfred W. Prais et al.

Page 1 of 1

It is certified that error appears in the above-identified patent and that said Letters Patent is hereby corrected as shown below:

On the Title Page

Item [72], Inventors, delete "Luedtka" and insert -- Luedtke --

Signed and Sealed this
Twenty-fifth Day of December, 2018

Andrei Iancu
*Director of the United States Patent and Trademark Office*